United States Patent
Coates et al.

(10) Patent No.: US 8,685,892 B2
(45) Date of Patent: Apr. 1, 2014

(54) COLORIMETRIC BIOASSAY FOR PERCHLORATE

(75) Inventors: John D. Coates, Walnut Creek, CA (US); Mark L. Heinnickel, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 153 days.

(21) Appl. No.: 13/062,052

(22) PCT Filed: Sep. 1, 2009

(86) PCT No.: PCT/US2009/055614
§ 371 (c)(1),
(2), (4) Date: Jul. 13, 2011

(87) PCT Pub. No.: WO2010/027977
PCT Pub. Date: Mar. 11, 2010

(65) Prior Publication Data
US 2011/0263440 A1    Oct. 27, 2011

Related U.S. Application Data

(60) Provisional application No. 61/093,979, filed on Sep. 3, 2008.

(51) Int. Cl.
*C40B 30/00* (2006.01)
*C40B 40/10* (2006.01)
*C12Q 1/26* (2006.01)

(52) U.S. Cl.
USPC .................................. 506/13; 435/25; 506/18

(58) Field of Classification Search
USPC .......................................................... 506/13
See application file for complete search history.

(56) References Cited

U.S. PATENT DOCUMENTS

2004/0137553 A1 *   7/2004   Coates et al. ................... 435/28

FOREIGN PATENT DOCUMENTS

WO    WO 2010/027977    3/2010

OTHER PUBLICATIONS

Bender et al., (Journal of Bacteriology, 2005, vol. 187, No. 15, pp. 5090-5096, Identification, Characterization, and Classification of Genes Encoding Perchlorate Reductase).*
Balk, M. et al., "(Per)chlorate reduction by the thermophillic Bacterium *Moorella perchloratireducens* sp. nov., Isolated from Underground Gas Storage", *App. Environ. Microbiol.*, vol. 74, No. 2, pp. 403-409 (2007).
Coates et al., "Microbial Perchlorate Reduction: Rocket-Fuelled Metabolism", *Nature Reviews*, vol. 2, pp. 569-580 (2004).
Okeke, B.C. et al., "Development of a perchlorate redctase-based biosensor for real time analysis of perchlorate in water", *J. of Microbiol. Methods*, vol. 68, Abstract (2006).

* cited by examiner

*Primary Examiner* — Ardin Marschel
*Assistant Examiner* — Richard L Manteuffel
(74) *Attorney, Agent, or Firm* — Morgan, Lewis & Bockius LLP; Jeffry S. Mann

(57) ABSTRACT

The present invention relates to methods, compositions and systems for detecting perchlorate in a sample. Compositions useful for detecting perchlorate in a sample include those comprising a perchlorate reductase, a reductant and an electron shuttle. In an exemplary embodiment, the composition comprises perchlorate reductase from *Dechloromonas agitata*, reduced nicotinamide adenine dinucleotide and N-methylphenazinium methylsulfate. The present invention also provides for methods of using the compositions disclosed herein, as well as systems thereof. In some exemplary embodiments, the methods comprise a concentration step, in which, for example, the sample is contacted with a cationic solid phase extraction column. Employing this step provides certain advantages such as a lowered detection limit and the removal of contaminants.

20 Claims, 2 Drawing Sheets

Figure 1 – Perchlorate detected by the colorimetric bioassay from 200 mL samples
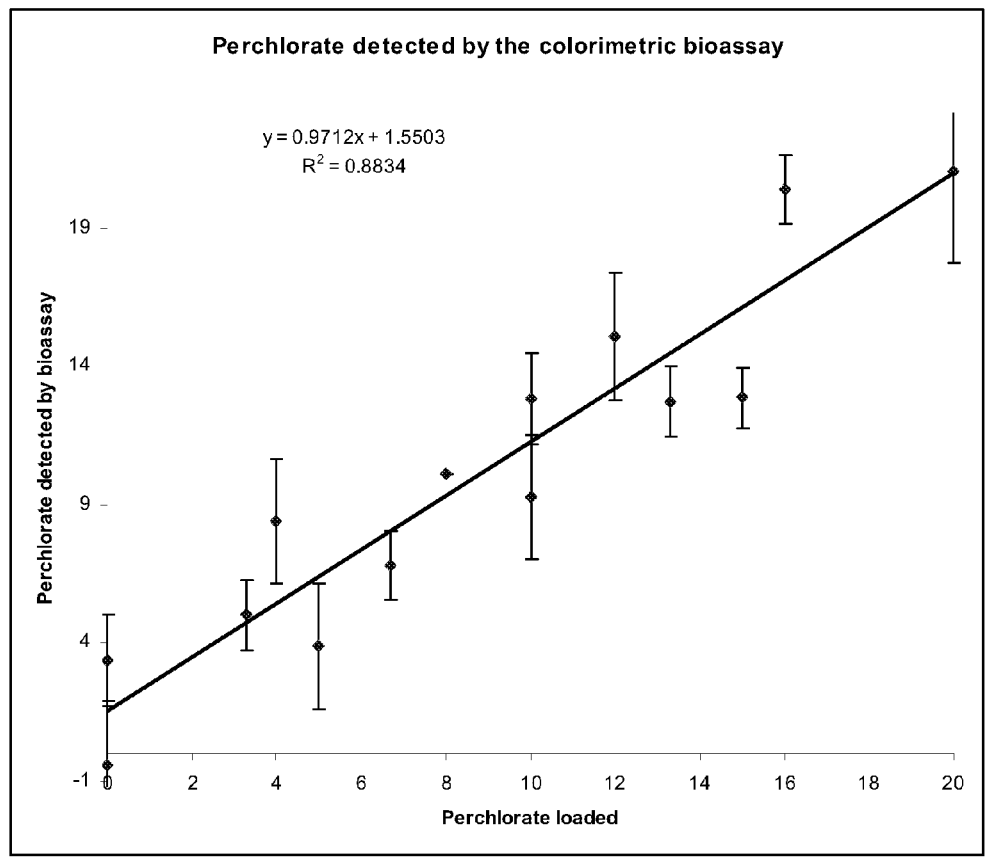

Figure 2 – Standard Curve generated in 2 M NaCl and 200 mM MOPS (pH 7)
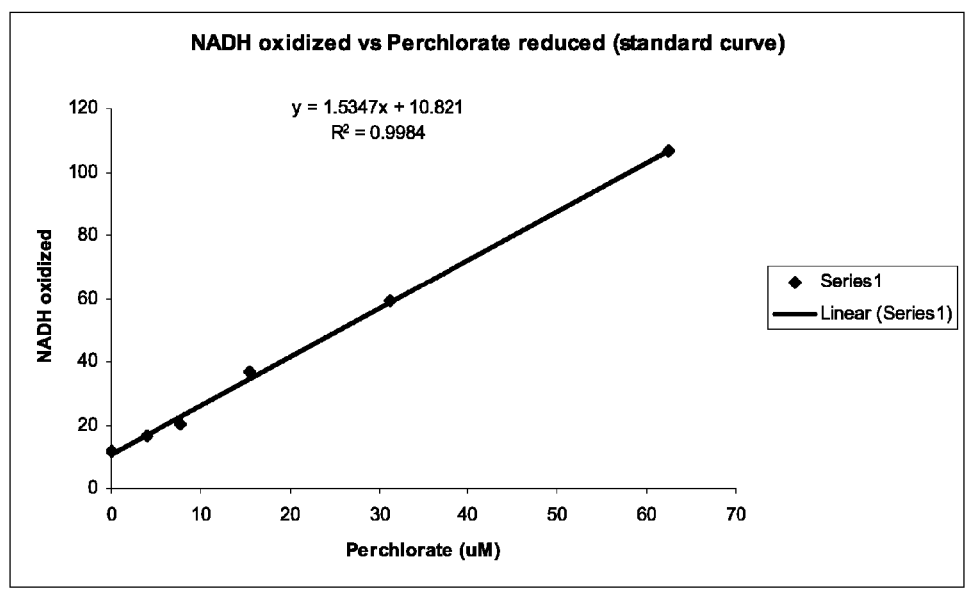

SEQUENCE LISTING

<160> NUMBER OF SEQ ID NOS: 2

<210> SEQ ID NO 1
<211> LENGTH: 927
<212> TYPE: PRT
<213> ORGANISM: Dechloromonas agitata

<400> SEQUENCE: 1

```
Met Ala Arg Leu Ser Arg Arg Asp Phe Leu Lys Ala Ser Ala Ala Thr
 1               5                  10                 15

Leu Leu Gly Asn Ser Leu Thr Phe Lys Thr Leu Ala Ala Thr Met Asp
             20                 25                 30

Leu Ser Gly Ala Phe Glu Tyr Ser Gly Trp Glu Asn Phe His Arg Asn
             35                 40                 45

Gln Trp Ser Trp Asp Lys Lys Thr Arg Gly Ala His Leu Ile Asn Cys
 50                 55                 60

Thr Gly Ala Cys Pro His Phe Val Tyr Thr Lys Asp Gly Val Val Ile
 65                 70                 75                 80

Arg Glu Glu Gln Ser Lys Asp Ile Pro Pro Met Pro Asn Ile Pro Glu
                 85                 90                 95

Leu Asn Pro Arg Gly Cys Asn Lys Gly Glu Cys Ala His His Tyr Met
             100                105                110

Tyr Gly Pro His Arg Leu Lys Tyr Pro Leu Ile Arg Val Gly Glu Arg
             115                120                125

Gly Glu Gly Lys Trp Arg Arg Ala Thr Trp Glu Glu Ala Leu Asp Leu
             130                135                140

Ile Ser Asp Lys Ile Ile Asp Thr Ile Lys Asn His Ser Pro Asp Cys
145                 150                155                160

Ile Ser Val Tyr Ser Pro Leu Pro Gly Thr Ala Pro Val Ser Phe Ser
             165                170                175

Ala Gly His Arg Phe Ala His Tyr Ile Gly Ala His Thr His Thr Phe
             180                185                190

Phe Asp Trp Tyr Ser Asp His Pro Thr Gly Gln Thr Gln Thr Cys Gly
             195                200                205

Val Gln Gly Asp Ser Ala Glu Cys Ser Asp Trp Phe Asn Ser Lys Tyr
             210                215                220

Ile Ile Leu Trp Gly Ala Asn Pro Thr Gln Thr Arg Ile Pro Asp Ala
225                 230                235                240

His Phe Leu Ser Glu Ala Gln Leu Asn Gly Ala Lys Val Val Ser Ile
             245                250                255

Ser Pro Asp Phe Asn Ser Ser Thr Ile Lys Ala Asp Arg Trp Ile His
             260                265                270

Pro Leu Pro Gly Thr Asp Gly Ala Leu Ala Leu Ala Met Ala His Val
             275                280                285

Ile Ile Lys Glu Lys Leu Tyr Asp Ala His Asn Leu Lys Glu Gln Thr
             290                295                300

Asp Leu Pro Tyr Leu Ile Arg Arg Asp Thr Lys Arg Phe Leu Arg Glu
305                 310                315                320

Ala Asp Val Val Ala Gly Gly Ser Lys Lys Phe Tyr Ile Trp Asp
             325                330                335

Ser Lys Thr Gly Lys Pro Val Ile Thr Lys Gly Ser Trp Gly Asp Gln
             340                345                350

Pro Glu Gln Lys Ala Pro Val Ala Phe Met Gly Arg Asn Thr His
             355                360                365

Thr Phe Pro Lys Gly Tyr Ile Ala Leu Glu Asn Leu Asp Pro Ala Leu
             370                375                380

Glu Gly Lys Phe Gln Val Lys Leu Gln Asp Gly Asn Thr Val Glu Val
385                 390                395                400

Arg Pro Val Phe Glu Ile Leu Lys Ser Arg Ile Glu Ala Asp Asn Asn
                 405                410                415

Ile Ala Lys Ala Ala Lys Ile Thr Gly Val Pro Ala Lys Thr Ile Ile
```

```
                420            425            430
    Glu Val Ala Arg Glu Tyr Ala Thr Thr Gln Pro Ala Met Ile Ile Cys
        435                440                445
    Gly Gly Gly Thr Met His Trp Tyr Tyr Ser Asp Val Leu Leu Arg Ala
        450                455                460
    Met His Leu Leu Thr Ala Leu Val Gly Ser Glu Gly Lys Asn Gly Gly
    465                470                475                480
    Gly Met Asn His Tyr Ile Gly Gln Trp Lys Pro Val Phe Leu Pro Gly
                    485                490                495
    Val Ala Ala Leu Ala Phe Pro Glu Gly Pro Ala Asn Glu Arg Ser Cys
                500                505                510
    Gln Thr Thr Ile Trp Thr Tyr Ile His Ala Glu Val Asn Asp Glu Met
                515                520                525
    Ala Asn Val Gly Ile Asp Thr Asp Lys Tyr Leu Met His Ala Ile Asp
                530                535                540
    Thr Arg Gln Met Pro Asn Tyr Pro Arg Asp Gly Arg Asp Pro Lys Val
    545                550                555                560
    Phe Ile Val Tyr Arg Gly Asn Trp Leu Asn Gln Ala Lys Gly Gln Lys
                    565                570                575
    Tyr Val Leu Arg Asn Leu Trp Pro Lys Leu Asp Leu Ile Val Asp Ile
                580                585                590
    Asn Ile Arg Met Asp Ser Thr Ala Leu Tyr Ser Asp Val Val Leu Pro
                595                600                605
    Ser Ala His Trp Tyr Glu Lys Leu Asp Leu Asn Val Thr Ala Glu His
                610                615                620
    Thr Tyr Ile Asn Met Thr Glu Pro Ala Ile Lys Pro Met Trp Glu Ser
    625                630                635                640
    Lys Thr Asp Trp Gln Ile Phe Leu Ala Leu Ala Lys Arg Val Glu Met
                    645                650                655
    Ser Ala Lys Arg Lys Ser Phe Glu Arg Phe Tyr Asp Glu Gln Phe Lys
                660                665                670
    Trp Ala Arg Asp Leu Thr Asn Leu Trp Asn Gln Met Thr Met Asp Gly
                675                680                685
    Lys Leu Ala Glu Asp Glu Ala Ala Gln Tyr Ile Leu Asp Thr Ala
                690                695                700
    Pro His Ser Lys Gly Ile Thr Leu Gln Met Leu Arg Glu Lys Gly Glu
    705                710                715                720
    Arg Phe Lys Ala Asn Trp Thr Ser Pro Met Lys Glu Gly Val Pro Tyr
                    725                730                735
    Thr Pro Phe Gln Asn Tyr Ile Val Asp Lys Lys Pro Trp Pro Thr Leu
                740                745                750
    Thr Gly Arg Gln Gln Phe Tyr Leu Asp His Glu Val Phe Phe Glu Met
                755                760                765
    Gly Val Glu Leu Pro Thr Tyr Lys Ala Pro Val Asp Ala Asp Lys Phe
                770                775                780
    Pro Phe Arg Phe Asn Ser Pro His Ser Arg His Ser Ile His Ser Thr
    785                790                795                800
    Phe Lys Asp Ser Val Leu Met Leu Arg Leu Gln Arg Gly Gly Pro Cys
                    805                810                815
    Val Glu Ile Ser Pro Ile Asp Ala Thr Ala Ile Gly Val Lys Asp Asn
                820                825                830
    Asp Trp Val Glu Ile Trp Asn Ser His Gly Lys Val Ile Cys Arg Ala
                835                840                845
```

```
Lys Ile Arg Ala Gly Glu Gln Arg Gly Arg Val Ser Met Trp His Thr
        850                 855                 860

Pro Glu Leu Tyr Met Asp Leu Leu Glu Gly Ser Thr Gln Ser Val Cys
865                 870                 875                 880

Pro Val Arg Ile Thr Pro Thr His Leu Val Gly Asn Tyr Gly His Leu
                    885                 890                 895

Val Phe Arg Pro Asn Tyr Tyr Gly Pro Ala Gly Ser Gln Arg Asp Val
                900                 905                 910

Arg Val Asp Val Lys Arg Tyr Ile Gly Ala Thr Pro Ile Ser Leu
                915                 920                 925

<210> SEQ ID NO 2
<211> LENGTH: 333
<212> TYPE: PRT
<213> ORGANISM: Dechloromonas agitata

<400> SEQUENCE: 2

Met Ser Asn Met Thr Lys Ser Pro Lys Arg Gln Leu Ala Tyr Val Ala
  1               5                  10                  15

Asp Leu Asn Lys Cys Ile Gly Cys Gln Thr Cys Thr Val Ala Cys Lys
                20                  25                  30

Thr Leu Trp Thr Ser Gly Pro Gly Gln Asp Tyr Met Tyr Trp Arg Asn
            35                  40                  45

Val Glu Thr Ala Pro Gly Leu Gly Tyr Pro Arg Asn Trp Gln Ser Lys
        50                  55                  60

Gly Gly Gly Tyr Lys Asp Gly Val Leu Gln Lys Gly Lys Ile Pro Pro
 65                 70                  75                  80

Met Ile Asp Tyr Gly Val Pro Phe Glu Phe Asp Tyr Ala Gly Arg Leu
                85                  90                  95

Phe Glu Gly Lys Lys Glu Arg Ala Arg Pro Ser Pro Thr Pro Arg Tyr
            100                 105                 110

Ala Pro Asn Trp Asp Glu Asp Gln Gly Ala Gly Glu Tyr Pro Asn Asn
        115                 120                 125

Ser Phe Phe Tyr Val Pro Arg Met Cys Asn His Cys Ala Lys Pro Ala
130                 135                 140

Cys Leu Glu Ala Cys Pro Asn Glu Ala Ile Tyr Lys Arg Glu Gln Asp
145                 150                 155                 160

Gly Leu Val Val Ile His Gln Glu Lys Cys Lys Gly Ala Gln Ala Cys
                165                 170                 175

Ile Gln Ser Cys Pro Tyr Ala Lys Pro Tyr Phe Asn Ala Gln Val Asn
            180                 185                 190

Lys Ala Asn Lys Cys Ile Gly Cys Phe Pro Arg Ile Glu Lys Gly Val
        195                 200                 205

Ala Pro Ala Cys Val Ala Glu Cys Ala Gly Arg Ala Met His Val Gly
    210                 215                 220

Phe Ile Asp Asp Gln Glu Ser Ser Val Phe Lys Leu Val Lys Arg Phe
225                 230                 235                 240

Gly Val Ala Leu Pro Leu His Pro Glu Tyr Gly Thr Glu Pro Asn Val
                245                 250                 255

Phe Tyr Val Pro Pro Val Leu Gly Pro Arg Val Glu Met Pro Asn Gly
            260                 265                 270

Glu His Thr Ala Asp Pro Lys Ile Ser Met Thr Gln Leu Glu Gln Leu
        275                 280                 285

Phe Gly Lys Gln Val Arg Glu Val Leu Lys Thr Leu Gln Ala Glu Arg
    290                 295                 300
```

```
Glu Lys Lys Ile Lys Asn Gln Pro Ser Glu Leu Met Asp Ile Leu Ile
305             310             315             320

Gly Arg Arg Ser Ala Asp Met Met Ile Ser Pro Met Thr
                325             330
```

COLORIMETRIC BIOASSAY FOR PERCHLORATE

CROSS-REFERENCE TO RELATED APPLICATIONS

This application is a National Stage under 35 U.S.C. 371 of PCT/US2009/055614 filed Sep. 1, 2009 which claims under 35 U.S.C. §119(e) the benefit of U.S. Patent Application No. 61/093,979 filed Sep. 3, 2008, the disclosure of which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant Number W912HQ-06-C-0026 awarded by the US Department of Defense ARO. The government has certain rights in the invention.

FIELD OF THE INVENTION

The present invention relates to methods, compositions and systems for detecting perchlorate in a sample.

BACKGROUND OF THE INVENTION

Recognition of perchlorate ($ClO_4^-$) as a widespread contaminant across the United States and its potential adverse affects towards human health has motivated the EPA to place $ClO_4^-$ on its contaminant candidate list for drinking water supplies. While a federal MCL has not yet been set, a recommended public health goal of 1 ppb ($\mu g \cdot L^{-1}$) was established by the US EPA in 2002. To date, methods of detection require use of sensitive ion chromatographic equipment that are expensive, time consuming, and require highly trained personnel for use. Our studies are focused on the development of a highly sensitive, simple, and robust colorimetric bioassay based on the primary enzyme involved in microbial $ClO_4^-$ reduction, the perchlorate reductase (Pcr).

A previously published assay used reduced methyl viologen (MV, the dye is reduced with sodium hydrosulfite) as an electron donor to demonstrate Pcr activity. The assay directly correlates the amount of MV oxidized with the amount of $ClO_4^-$ reduced by assuming a transfer of four electrons. To test this assumption, we compared actual concentrations of MV oxidized to $ClO_4^-$ reduced in this assay. $ClO_4^-$ concentrations were determined using a Dionex ICS-1500 ion chromatography system, while MV concentrations were determined using a standard curve generated at 578 nm. Comparisons between the two revealed that twelve molecules of MV are oxidized for each molecule of $ClO_4^-$ reduced. The oxidation of these additional eight MV molecules is explained by the interaction of the dye with chlorite (the product of the Pcr reaction) and other contaminants that could be present in the enzyme prep. This unsettling result indicated this assay would be problematic for the detection of $ClO_4^-$ in soil, which has many chemicals that could react with MV.

To improve upon this assay, we have tried to reduce $ClO_4^-$ using less reactive dyes and reductants. The reductants ascorbic acid, NADH, and dithiothreitol drive Pcr catalyzed $ClO_4^-$ reduction, however, they are not effective unless an accompanying dye is used as a shuttle. N-methylphenazinium methosulfate (PMS) was selected as the most suitable dye because of its interaction with NADH, an oxygen stable reductant. In addition, the positive redox potential of PMS ($E°=+80$ mV), makes it significantly less reactive than MV ($E°=-450$ mV). A comparison of actual concentrations of $ClO_4^-$ reduced vs. NADH oxidized show approximately four molecules of NADH oxidized for each molecule of $ClO_4^-$ that is reduced (8 electrons).

These studies have resulted in the successful development of a method that can accurately determine $ClO_4^-$ concentrations with a small error using the enzyme Pcr and indicate the great potential for the ultimate development of a simple, robust, and highly sensitive colorimetric bioassay for perchlorate that can be widely used to screen laboratory and environmental samples.

BRIEF DESCRIPTION OF THE DRAWINGS

FIG. 1 shows the detection of perchlorate by the colorimetric bioassay described herein.

FIG. 2 shows a standard curve for the amount of NADH oxidized versus perchlorate reduced.

DETAILED DESCRIPTION OF THE INVENTION

The present invention provides compositions and methods for a bioassay for detecting perchlorate. In one embodiment, the bioassay is based on the activity of the novel perchlorate reductase enzyme purified from the perchlorate-respiring microorganism *Dechloromonas agitata*. This enzyme reduces perchlorate ($ClO_4^-$) or chlorate ($ClO_3^-$) to chlorite ($ClO_2^-$) in the presence of reduced nicotinamide adenine dinucleotide (NADH) as a suitable electron donor with n-methylphenazinium methosulfate (PMS) as an electron shuttle. The oxidation of the NADH to $NAD^+$ is proportional to the original perchlorate concentration in the sample and can be monitored spectrophotometrically by absorbance change at 340 nm. When combined with a simple solid phase extraction procedure the assay is specific for perchlorate and has a predicted sensitivity in the order of 400 ppt.

Current assay procedures for perchlorate are based on ion chromatography using conductivity detection. These assay procedures achieve detection limits in the order of 4 ppb but are limited by the cost and complexity requiring specialized equipment and highly trained personnel. They are also limited by the sequential nature of the analysis, in that samples must be analyzed individually. The simple colorimetric assay outlined herein overcomes all of these issues in that it can achieve similar detection limits at a significantly lower cost, and can be performed in the field by personnel with limited training and basic (low cost) laboratory equipment. Furthermore, the colorimetric assay allows for the simultaneous processing of multiple samples (up to 96 in a spectrophotometer equipped with a microplate reader).

In one aspect, the present invention provides compositions comprising (a) a perchlorate reductase (PCR), (b) a reductant and (c) an electron shuttle.

The term "perchlorate reductase" or "PCR" refers to an enzyme that catalyzes the reduction of perchlorate ($ClO_4^-$) or chlorate ($ClO_3^-$) to chlorite ($ClO_2^-$). Perchlorate reductases useful for the present invention can be derived from a number of different organisms such as bacteria. In one embodiment, the perchlorate reductase is derived from a bacterium of the genus *Dechloromonas*. In an exemplary embodiment, the perchlorate reductase is derived from the bacterial species *Dechloromonas agitata*. Perchlorate reductase from *Dechloromonas agitata* comprises two subunits, PcrA (GenBank Accession Number AAO49008; SEQ ID NO: 1) and PcrB (GenBank Accession Number AAY27748; SEQ ID NO: 2), encoded by the genes pcrA and pcrB respectively.

```
SEQ ID NO: 1 (GenBank Accession Number AAO49008)
MARLSRRDFL KASAATLLGN SLTFKTLAAT MDLSGAFEYS GWENFHRNQW SWDKKTRGAH

LINCTGACPH FVYTKDGVVI REEQSKDIPP MPNIPELNPR GCNKGECAHH YMYGPHRLKY

PLIRVGERGE GKWRRATWEE ALDLISDKII DTIKNHSPDC ISVYSPLPGT APVSFSAGHR

FAHYIGAHTH TFFDWYSDHP TGQTQTCGVQ GDSAECSDWF NSKYIILWGA NPTQTRIPDA

HFLSEAQLNG AKVVSISPDF NSSTIKADRW IHPLPGTDGA LALAMAHVII KEKLYDAHNL

KEQTDLPYLI RRDTKRFLRE ADVVAGGSKD KFYIWDSKTG KPVITKGSWG DQPEQKAPPV

AFMGRNTHTF PKGYIALENL DPALEGKFQV KLQDGNTVEV RPVFEILKSR IEADNNIAKA

AKITGVPAKT IIEVAREYAT TQPAMIICGG GTMHWYYSDV LLRAMHLLTA LVGSEGKNGG

GMNHYIGQWK PVFLPGVAAL AFPEGPANER SCQTTIWTYI HAEVNDEMAN VGIDTDKYLM

HAIDTRQMPN YPRDGRDPKV FIVYRGNWLN QAKGQKYVLR NLWPKLDLIV DINIRMDSTA

LYSDVVLPSA HWYEKLDLNV TAEHTYINMT EPAIKPMWES KTDWQIFLAL AKRVEMSAKR

KSFERFYDEQ FKWARDLTNL WNQMTMDGKL AEDEAAAQYI LDTAPHSKGI TLQMLREKGE

RFKANWTSPM KEGVPYTPFQ NYIVDKKPWP TLTGRQQFYL DHEVFFEMGV ELPTYKAPVD

ADKFPFRFNS PHSRHSIHST FKDSVLMLRL QRGGPCVEIS PIDATAIGVK DNDWVEIWNS

HGKVICRAKI RAGEQRGRVS MWHTPELYMD LLEGSTQSVC PVRITPTHLV GNYGHLVFRP

NYYGPAGSQR DVRVDVKRYI GATPISL

SEQ ID NO: 2 (GenBank Accession Number AAY27748)
MSNMTKSPKR QLAYVADLNK CIGCQTCTVA CKTLWTSGPG QDYMYWRNVE TAPGLGYPRN

WQSKGGGYKD GVLQKGKIPP MIDYGVPFEF DYAGRLFEGK KERARPSPTP RYAPNWDEDQ

GAGEYPNNSF FYVPRMCNHC AKPACLEACP NEAIYKREQD GLVVIHQEKC KGAQACIQSC

PYAKPYFNAQ VNKANKCIGC FPRIEKGVAP ACVAECAGRA MHVGFIDDQE SSVFKLVKRF

GVALPLHPEY GTEPNVFYVP PVLGPRVEMP NGEHTADPKI SMTQLEQLFG KQVREVLKTL

QAEREKKIKN QPSELMDILI GRRSADMMIS PMT
```

The term "perchlorate reductase" or "PCR" includes perchlorate reductase and variants thereof. A variant of a protein such as perchlorate reductase has one or more peptide additions, deletions or substitutions compared to another protein, often compared to the wild-type sequence of the protein. The term "perchlorate reductase" or "PCR" also includes chemical modifications of any peptide, including but not limited to glycosylation and phosphorylation. A perchlorate reductase may optionally include one or more nonstandard amino acids as are known in the art. Thus, in one embodiment, the perchlorate reductase is an enzyme that catalyzes the reduction of perchlorate to chlorite and has at least 80%, at least 90%, at least 95%, at least 96%, at least 97%, at least 98% or at least 99% sequence identity to a wild-type perchlorate reductase, such as for example perchlorate reductase expressed by Dechloromonas agitata.

In one embodiment, the perchlorate reductase catalyzes the reduction of perchlorate ($ClO_4^-$) or chlorate ($ClO_3^-$) to chlorite ($ClO_2^-$) and has at least 80%, at least 90%, at least 95%, at least 96%, at least 97%, at least 98% or at least 99% or 100% sequence identity to a perchlorate reductase comprising a first subunit having a sequence according to SEQ ID NO: 1 and a second subunit having a sequence according to SEQ ID NO: 2.

As described herein, perchlorate reductase may be expressed in and extracted from an organism including but not limited to a bacterial species such as Dechloromonas agitata. Methods for expression and extraction are well-known in the art. In one embodiment, perchlorate reductase is isolated, that is, separated from different molecules such that a population of perchlorate reductase is at least 90%, at least 95%, at least 96%, at least 97%, at least 98%, at least 99% or 100% homogenous. In some embodiments, perchlorate reductase is partially purified, that is, a population of perchlorate reductase may include molecules other than perchlorate reductase (including but not limited to other molecules from a bacterial cell) such that the population of perchlorate reductase is less than 90% homogenous.

The term "reductant" refers to any species that can be oxidized, that is, any species that can donate an electron to another species such as an oxidant. In one embodiment, the reductant donates an electron to an electron shuttle such as PMS. In one embodiment, the reductant is a labile one- or two-electron donor having a redox potential less than +80 mV. Examples of labile donors include but are not limited to dithionite, hydride donors, quinones, and thiols. Reductants that are useful in the present invention include those whose molar absorptivity is well characterized. Thus, in an exemplary embodiment, the reductant is reduced nicotinamide adenine dinucleotide (NADH). Other reductants may include ascorbic acid or dithiothreitol.

The term "electron shuttle" refers to a species that is reduced by a reductant as described herein and which in turn acts as a reductant to a perchlorate reductase. In one embodiment, the electron shuttle comprises a substituted or unsubstituted phenazine moiety. In one embodiment, the phenazine moiety is substituted with a substituted or unsubstituted alkyl group. In some embodiments, the phenazine moiety is substituted with a substituted or unsubstituted lower alkyl (that is, $C_1$ to $C_6$), and in some embodiments, the lower alkyl is methyl. In an exemplary embodiment, the electron shuttle is N-methylphenazinium methylsulfate (PMS). A number of characteristics make PMS a useful electron shuttle. First, it is oxygen stable. Second PMS is an amphiphile, that is, a molecule that is both hydrophobic and hydrophilic. This characteristic allows PMS to be soluble in water (a hydrophilic environment), but quickly donate electron to the inside of proteins (a hydrophobic environment). Third, PMS can oxidize many reductants including thiols, ascorbic acid, dithionite, and NADH.

In one aspect, the present invention provides methods of detecting perchlorate in a sample using a composition described herein.

The term "sample" includes but is not limited to an aqueous solution. A sample may also comprise a fluid obtained from a host, for example, urine, whole blood, plasma, serum, saliva, semen, stool, sputum, cerebral spinal fluid, tears, mucus, breast milk or the like. Optionally, the sample may be pretreated and may be prepared in any convenient medium that does not interfere with the assay. In some embodiments, the sample comprises matter such as soil.

The term "detecting" or "detection" refers to determining the existence of an entity such as a chemical compound. The detection of a compound can be direct or indirect and can be the result of a qualitative or quantitative measurement. In one embodiment, detecting a molecule refers to determining the absence or presence of a molecule in a sample. In one embodiment, detecting a molecule refers to measuring the amount of molecule in a sample or measuring the activity of the molecule in a sample. Thus, in one aspect, the invention provides methods of determining the presence and/or quantity of perchlorate in a sample.

In some embodiments, detecting a first molecule (such as for example perchlorate) is indirect, that is, achieved through detecting a second molecule. In an exemplary embodiment, detecting perchlorate is achieved through detecting a reductant such as NADH.

The present invention contemplates the use of a number of different detection systems. In one embodiment, the detection system includes the use of optical spectroscopy as is known in the art. In an exemplary embodiment, the method of detecting perchlorate comprises the measurement of optical absorbance.

Another aspect of the present invention relates to kits useful for conveniently determining the presence or the concentration of perchlorate in a sample. The kits may comprise any of the compositions disclosed herein. In one embodiment, the kits can further comprise calibration and control standards useful in performing the assay, or ancillary reagents. The reagents may each be in separate containers, or various reagents can be combined in one or more containers depending on cross-reactivity and stability of the reagents. In one embodiment, the kits further comprise instructions for using the kit.

Assay

An aerobic colorimetric bioassay for the determination of parts per billion (ppb) concentrations of perchlorate has been developed and is described herein. The assay uses the enzyme perchlorate reductase (PCR) in purified and partially purified forms to detect perchlorate. The redox active dye phenazine methosulfate (PMS) can efficiently shuttle electrons to PCR. Because PMS can oxidize NADH, perchlorate can be determined indirectly by monitoring NADH oxidization by PCR. By using a specific addition scheme and covering all reactions with mineral oil, this reaction can proceed aerobically on the benchtop, and has a lower detection limit of 200 ppb. In order to lower the detection limit of this assay and remove any interfering components, we have shown that perchlorate can be concentrated on a solid phase extraction (SPE) column that is pre-treated with the cation decyltrimethylammonium bromide (DTAB). Perchlorate has been previously shown to elute from these columns with 1 mL of acetone. However, we have found that acetone interferes with our bioassay, and have substituted it with a solution of 2 M NaCl and 200 mM MOPS (pH 12.5). By washing these columns with 15 mL of 2.5 mM DTAB and 15% Acetone, we have found that we can elute contaminating ions, such as chlorate and nitrate, without eluting perchlorate. This bioassay will allow us to detect perchlorate in environmentally important concentrations (2 ppb) in the field. Common groundwater contaminants should have no effect on this assay.

Methods

Cleaning and Conditioning the SPE Column

Using a 60 mL syringe with an attached tygon tube, push 10 mL of acetone followed by 30 mL of air through a Phenomenex styrene divinyl benzene SPE column. Dispose of all acetone washings in an appropriate manner.

Using the same 60 mL syringe, push 20 mL of water through the column followed by 30 mL of air to remove residual acetone.

Following these rinse steps, ensure that the frit on top of the column is pushed tight against the resin bed. This can be checked using a 1 mL syringe.

Add 1 mL of 25 mM decyltrimethylammonium bromide (DTAB) to the Phenomenex styrene divinyl benzene column (SDVB columns). Slowly push this liquid through the column using the 60 mL syringe. The flow rate should be approximately 1 drop per second.

Once the DTAB has been pushed through the column, push an additional 20 mL of air through the column to remove any residual solution.

Loading/Eluting the SPE Columns

Pass 100-500 mL of perchlorate containing solution (sample or standard) through the prewashed column. This can be automated with a multihead pressure manifold or performed by hand injection. Flow rate is very important during the loading step. Try and let the liquid flow through the columns at a slow rate. A stream of consistent drops is better than a constant stream.

Once loaded, wash the columns with 7.5 mL of 2.5 mM DTAB and 15% acetone solution. This solution will elute chlorate and nitrate, but not perchlorate. Push this solution through the column slowly with the syringe.

Elute perchlorate from the columns using 2 mL of solution of 2 M NaCl and 200 mM MOPS (pH 13). Push this high salt solution through the column slowly at a rate of approximately 1 drop per second. Collect the eluant solution in 10×75 mm glass tubes.

Neutralize the solution by adding 300 μL of a 1 M HCl solution. The final pH of the solution should be 7-7.5 (this pH can be verified using pH paper).

(Columns can be recycled for future use by passing 3 mL of $ddH_2O$ through the SDVB columns to remove any residual MOPS and NaCl. These chemicals can clog the columns during the initial acetone rinse used to prepare the columns.

Colorimetric Bioassay for Perchlorate

The colorimetric bioassay can be done in either aerobic or anaerobic conditions. The protocol below details the procedure done under aerobic conditions. However, if the mineral step is removed this same protocol can be used in anaerobic chamber in microplate reader or cuvettes.

Put 1 mL of the prepared sample or standard into 2 mL quartz cuvette with a path length of 1 cm. The sample (if concentrated on the SDVB columns) should have a concentration of 2 M NaCl and 200 mM MOPS (pH ~7).

1 mL of mineral oil is placed on top of the cuvette. This mineral oil acts as a cap to keep oxygen out of the sample.

Add Phenazine Methosulfate (PMS) to a final concentration of 175 μM to the sample underneath the mineral oil. The addition of PMS should turn the sample yellow in color. If the sample is green, the PMS has degraded and needs to be replaced with a fresh solution. If the sample is either blue or red, the pH is not 7 and needs to be corrected before continuing.

Add NADH to a final concentration of 500 μM to the sample underneath the mineral oil. Mix the solution thoroughly with a micropippetor. Following the mixing, the sample should turn from yellow to clear or slightly cloudy. If the NADH is not active, the sample will not change color. Allow the sample to sit in the dark for 5 minutes following this addition.

Add 1 unit of enzyme to the assay mixture to the sample underneath the mineral oil. If the enzyme includes chlorite dismutase, 1 unit is the amount of enzyme required to oxidize 4 μM NADH/min in the presence of saturating amounts of perchlorate. If the enzyme prep is free of chlorite dismutase, then one unit of activity is the amount of enzyme required to oxidize 2 μM NADH/min in the presence of saturating amounts of perchlorate.

Incubate the samples at 30° C. in the dark and measure the absorbance at 340 nm after 20 mins. Concentration of perchlorate in the sample can be calculated by comparison of the absorbance against that of a similar assay performed with an authentic standard.

Exemplary embodiments are summarized herein below.

In an exemplary embodiment, the invention provides a composition comprising (a) a perchlorate reductase (PCR), (b) a reductant and (c) an electron shuttle.

In an exemplary embodiment, according to the above paragraph, the electron shuttle comprises a substituted or unsubstituted phenazine moiety.

In an exemplary embodiment, according to any of the above paragraphs, the electron shuttle is N-methylphenazinium methylsulfate (PMS).

In an exemplary embodiment, according to any of the above paragraphs, the reductant is reduced nicotinamide adenine dinucleotide (NADH).

In an exemplary embodiment, according to any of the above paragraphs, the perchlorate reductase has at least 90% sequence identity to a perchlorate reductase derived from *Dechloromonas agitata*.

In an exemplary embodiment, according to any of the above paragraphs, the perchlorate reductase has at least 90% sequence identity to a perchlorate reductase comprising a first subunit having a sequence according to SEQ ID NO: 1 and a second subunit having a sequence according to SEQ ID NO: 2.

In an exemplary embodiment, according to any of the above paragraphs, the PCR is partially purified.

In an exemplary embodiment, according to any of the above paragraphs, the PCR is isolated.

In an exemplary embodiment, the invention provides a method of determining the presence or quantity of perchlorate in a sample comprising: (a) contacting the sample with the composition of any of the preceding claims; and (b) applying spectroscopy to the sample, thereby determining the presence or quantity of perchlorate in a sample.

In an exemplary embodiment, according to the above paragraph, the method further comprises contacting the sample with a cationic solid phase extraction column.

In an exemplary embodiment, according to any of the above paragraphs, the extraction column is pretreated with a quaternary ammonium bromide surfactant.

In an exemplary embodiment, according to any of the above paragraphs, the quaternary ammonium bromide surfactant is decyltrimethylammonium bromide (DTAB).

In an exemplary embodiment, according to any of the above paragraphs, the method further comprises eluting the perchlorate by contacting the extraction column with a solution comprising NaCl and 3-(N-morpholino)propanesulfonic acid (MOPS).

In an exemplary embodiment, according to any of the above paragraphs, the sample comprises a contaminating ion, and the method further comprises eluting the contaminating ion by contacting the extraction column with a solution comprising DTAB and acetone.

In an exemplary embodiment, according to any of the above paragraphs, the method has a detection limit of at least about 2 ppb.

In an exemplary embodiment, according to any of the above paragraphs, the method has a detection limit of at least about 10, at least about 50, at least about 100 or at least about 200 ppb.

In an exemplary embodiment, according to any of the above paragraphs, the spectroscopy comprises the measurement of optical absorbance.

In an exemplary embodiment, according to any of the above paragraphs, the sample comprises an aqueous solution.

In an exemplary embodiment, according to any of the above paragraphs, the sample comprises soil.

In an exemplary embodiment, according to any of the above paragraphs the sample is part of a sample array.

In an exemplary embodiment, the invention provides a kit comprising the composition described in any of the above paragraphs, and instructions for using the composition.

In an exemplary embodiment, the invention provides a system for detecting perchlorate in a plurality of samples comprising a solid support comprising an array of detection sites, wherein at least one of the detection sites comprises the composition described in any of the above paragraphs.

The invention is further illustrated by the Examples that follow. The Examples are not intended to define or limit the scope of the invention.

EXAMPLES

Example 1

Analyzing Samples Concentrated on the SPE Columns

Perchlorate concentrations were brought to 0-20 ppb in two hundred milliliter samples of ddH$_2$O. These samples were loaded onto SPE columns that were cleaned with acetone and ddH$_2$O. The SPE columns were also equilibrated with 1 mL of 25 mM DTAB. The samples were pushed through the columns using nitrogen gas pressure (~10 psi) in a multihead manifold. Following the loading step all residual liquid was pushed through the columns using a 60 mL syringe. Perchlorate was eluted from the column using 2 mL of a 2 M NaCl and 200 mM MOPS (pH 12.5) solution. Following the elution the samples were neutralized by adding 300 µL 1 N HCl. An approximate pH of 7.5-8.0 was determined using pH paper. Following the elution, samples were analyzed in the anaerobic chamber.

280 µL of sample were incubated with 175 µM PMS and 500 µM NADH. Once the absorbance at 340 nm stabilized (~10 min) 3 µL of whole cell lysate was added to the sample. The reaction was allowed to proceed for 60 min. Following this reaction, the amount of NADH that was oxidized by Perchlorate reductase was calculated by determining the absorbance change at 340 nm. Perchlorate concentrations were determined using a standard curve that was generated in neutralized elution buffer (200 mM MOPS, 2M NaCl). FIG. 1 shows the determined values.

Example 2

Purifying Perchlorate from Anionic Contaminants

As described above, 200 mL samples were loaded onto SPE columns that were preconditioned with decyltrimethylammonium bromide. The 200 mL samples were spiked with the indicated concentrations of perchlorate, as well as the contaminants listed in Table 1.

TABLE 1

Bioassay determination of perchlorate in samples co-contaminated with 100 ppm nitrate or 1 ppm chlorate

| Actual Concentration (ppb) | ddH$_2$O (no co-contaminants) | 100 ppm Nitrate | 1 ppm Chlorate |
|---|---|---|---|
| 0 | −1.86 | 1.09 | −0.93 |
| 5 | 4.51 | 3.76 | 3.82 |
| 10 | 10.53 | 6.72 | 6.38 |
| 15 | 14.30 | 16.35 | 12.21 |
| 20 | 18.91 | 21.87 | 17.95 |

It was found experimentally that nitrate could be added to a final concentration of 100 ppm and eluted to a non-interfering concentration with 7.5 mL of 15% acetone and 2.5 mM DTAB. Nitrate was selected as a contaminant of study because it is a common groundwater anion, and was shown previously to interact with perchlorate reductase. Perchlorate concentrations were determined using a standard curve generated using the bioassay (FIG. 2). The standards, like the samples, were made in elution buffer (2 M NaCl and 200 mM MOPS (pH 7)). As can be seen below, nitrate, even at molar excess of 7,500 to 30,000, does not interfere with the detection of perchlorate.

Chlorate, the only molecule known to react more readily with perchlorate reductase than perchlorate, was brought to a final concentration of 1 ppm in samples also spiked with the indicated values of perchlorate. The majority of the chlorate could be removed from the SPE columns with a 15 mL wash of 15% acetone and 2.5 mM DTAB. There was some residual chlorate remaining, but this chlorate reacts quickly with the enzyme that is added, and before the enzyme reacts with perchlorate. In order to negate this small contamination, the enzyme is allowed to incubate with the samples for 10 minutes before any measurements are taken. In this time, all of the chlorate reacts with the enzyme first, and does not interfere with perchlorate determination.

Example 3

Determining Perchlorate Concentrations in Contaminated Groundwater Samples

Four groundwater samples were acquired from a perchlorate-contaminated site in Sacramento, Calif. with approximate contaminations of perchlorate (shown in parentheses by sample identification number). The actual perchlorate concentrations were determined by both ion chromatography and the colorimetric bioassay following a concentration on the SPE columns (with the exception of the sample ID# 4703, which was analyzed following a 10 fold dilution in eluting buffer). In both techniques, perchlorate concentrations were determined using standard curves generated from a purchased perchlorate stock. The results are shown in Table 2.

TABLE 2

Perchlorate determined from various environmental groundwater samples collected from a known perchlorate-contaminated site in California.

| Sample Identification# | Average (ion chromatography) | St. Dev. (ion chromatography) | Average (Bioassay) | St. Dev (Bioassay) |
|---|---|---|---|---|
| 7069 (~6 ppb) | 1.93 ppb | 0.68 | −0.78 ppb | 1.01 |
| 4590 (~20 ppb) | 8.17 ppb | 0.32 | 8.44 ppb | 0.43 |
| 4830 (~100 ppb) | 20.21 ppb | 1.99 | 22.95 ppb | 1.56 |
| 4703 (~30 ppm) | 16.73 ppm | 5.46 | 19.74 ppm | 2.83 |

In some samples, detection of perchlorate may be enhanced if the SPE columns concentrated the perchlorate samples more than 100 fold. Perchlorate concentrations in parentheses under the sample identification # were previously determined prior to our sample collection and analysis.

The preceding examples are offered by way of illustration and not by way of limitation. It should be apparent that the invention can include additional embodiments not illustrated by example.

The articles "a," "an" and "the" as used herein do not exclude a plural number of the referent, unless context clearly dictates otherwise. The conjunction "or" is not mutually exclusive, unless context clearly dictates otherwise.

All references, publications, patent applications, issued patents, molecular sequences and database accession records cited herein are incorporated by reference in their entirety for all purposes.

We claim:

1. A composition comprising: (a) a perchlorate reductase (PCR), (b) a reductant, and (c) an electron shuttle wherein the electron shuttle comprises an unsubstituted phenazine moiety or N-methylphenazinium methylsulfate (PMS).

2. The composition of claim 1 wherein the reductant is reduced nicotinamide adenine dinucleotide (NADH).

3. The composition of claim 1 wherein the perchlorate reductase has at least 90% sequence identity to a perchlorate reductase derived from *Dechloromonas agitata*.

4. The composition of claim 3 wherein the perchlorate reductase has at least 90% sequence identity to a perchlorate reductase comprising a first subunit having a sequence according to SEQ ID NO: 1 and a second subunit having a sequence according to SEQ ID NO: 2.

5. The composition of claim 1 wherein the PCR is a member selected from partially purified PCR and isolated PCR.

6. A method of determining the presence or quantity of perchlorate in a sample comprising:
   (a) contacting the sample with the composition of claim 1; and
   (b) submitting the sample to spectroscopic analysis, thereby determining the presence or quantity of perchlorate in a sample.

7. The method of claim 6 further comprising contacting the sample with a cationic solid phase extraction column.

8. The method of claim 7 wherein the extraction column is pretreated with a quaternary ammonium bromide surfactant.

9. The method of claim 8 wherein the quaternary ammonium bromide surfactant is decyltrimethylammonium bromide (DTAB).

10. The method of claim 7 further comprising eluting the perchlorate by contacting the extraction column with a solution comprising NaCl and 3-(N-morpholino)propanesulfonic acid (MOPS).

11. The method of claim 7 wherein the sample comprises a contaminating ion, the method further comprising eluting the contaminating ion by contacting the extraction column with a solution comprising DTAB and acetone.

12. The method of claim 6 wherein the method has a detection limit of at least about 2 ppb.

13. The method of claim 6 wherein the method has a detection limit of at least about 10, at least about 50, at least about 100 or at least about 200 ppb.

14. The method of claim 6 wherein the spectroscopy comprises the measurement of optical absorbance.

15. The method of claim 6 wherein the sample comprises an aqueous solution.

16. The method of claim 6 wherein the sample comprises soil.

17. The method of claim 6 wherein the sample is part of a sample array.

18. A kit comprising the composition of claim 1 and instructions for using the composition.

19. A system for detecting perchlorate in a plurality of samples comprising a solid support comprising an array of detection sites, wherein at least one of the detection sites comprises the composition of claim 1.

20. A composition comprising: (a) a perchlorate reductase (PCR), (b) a reductant, and (c) an electron shuttle wherein the electron shuttle comprises a phenazine moiety, substituted with a substituted or unsubstituted alkyl group.

* * * * *